(12) United States Patent
Sato et al.

(10) Patent No.: US 8,915,840 B2
(45) Date of Patent: Dec. 23, 2014

(54) CAPSULE-TYPE MEDICAL DEVICE, POWER SUPPLY APPARATUS, AND POWER SUPPLY SYSTEM

(75) Inventors: Ken Sato, Nagano (JP); Hiroshi Iwaisako, Shiojiri (JP); Hideharu Miyahara, Nagano (JP); Naoki Yoshida, Nagano (JP)

(73) Assignee: Olympus Corporation, Tokyo (JP)

( * ) Notice: Subject to any disclaimer, the term of this patent is extended or adjusted under 35 U.S.C. 154(b) by 312 days.

(21) Appl. No.: 13/108,339

(22) Filed: May 16, 2011

(65) Prior Publication Data

US 2011/0218402 A1   Sep. 8, 2011

Related U.S. Application Data

(63) Continuation of application No. PCT/JP2009/068423, filed on Oct. 27, 2009.

(30) Foreign Application Priority Data

Nov. 18, 2008   (JP) ................................. 2008-294794
Nov. 20, 2008   (JP) ................................. 2008-297042

(51) Int. Cl.
| | | |
|---|---|---|
| A61B 1/04 | (2006.01) | |
| A61B 1/00 | (2006.01) | |
| A61B 6/00 | (2006.01) | |
| H02J 5/00 | (2006.01) | |
| A61B 6/03 | (2006.01) | |

(52) U.S. Cl.
CPC ......... *A61B 1/00016* (2013.01); *A61B 1/00029* (2013.01); *A61B 1/041* (2013.01); *A61B 6/56* (2013.01); *H02J 5/005* (2013.01); *A61B 1/00027* (2013.01); *A61B 6/032* (2013.01); *A61B 2560/0214* (2013.01)

USPC .......... 600/118; 600/101; 307/104; 333/17.1; 333/17.3

(58) Field of Classification Search
CPC ........................ A61B 1/00027; A61B 1/00029
USPC .......... 600/118, 109, 130, 160, 101; 307/104; 340/539.12; 333/32, 17.3, 17.1
See application file for complete search history.

(56) References Cited

U.S. PATENT DOCUMENTS 5,831,348 A  * 11/1998  Nishizawa ................... 307/104
6,424,232 B1 *  7/2002  Mavretic et al. ............ 333/17.3

(Continued)

FOREIGN PATENT DOCUMENTS

| EP | 1 952 753 A1 | 8/2008 |
|---|---|---|
| JP | 2004-72832 A | 3/2004 |

(Continued)

OTHER PUBLICATIONS

Abstract of Japanese Patent Publication No. 2001-231186, dated Aug. 24, 2001.

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

Provided is a capsule-type endoscope that has a power receiving coil that wirelessly receives an electric power from outside a body of an individual to be examined, a processing circuit that performs predetermined processing, and an adjusting reactance section that is capable of adjusting a reactance that is connected to the power receiving coil.

14 Claims, 12 Drawing Sheets

(56) References Cited

U.S. PATENT DOCUMENTS

| | | | |
|---|---|---|---|
| 6,427,065 B1* | 7/2002 | Suga et al. | 455/41.1 |
| 6,591,139 B2* | 7/2003 | Loftin et al. | 607/60 |
| 6,772,011 B2* | 8/2004 | Dolgin | 607/61 |
| 7,256,695 B2* | 8/2007 | Hamel et al. | 340/572.1 |
| 2003/0218514 A1* | 11/2003 | Eckl et al. | 333/32 |
| 2004/0113790 A1 | 6/2004 | Hamel et al. | |
| 2005/0065407 A1* | 3/2005 | Nakamura et al. | 600/160 |
| 2005/0143647 A1* | 6/2005 | Minai et al. | 600/410 |
| 2005/0146220 A1* | 7/2005 | Hamel et al. | 307/44 |
| 2008/0157603 A1* | 7/2008 | Baarman et al. | 307/104 |
| 2008/0177143 A1* | 7/2008 | Yoshida et al. | 600/130 |
| 2009/0243397 A1* | 10/2009 | Cook et al. | 307/104 |
| 2010/0213770 A1* | 8/2010 | Kikuchi | 307/104 |
| 2011/0025132 A1* | 2/2011 | Sato | 307/104 |
| 2011/0101788 A1* | 5/2011 | Sun et al. | 307/104 |
| 2011/0101790 A1* | 5/2011 | Budgett | 307/104 |
| 2011/0193416 A1* | 8/2011 | Campanella et al. | 307/104 |
| 2011/0210621 A1* | 9/2011 | Iwaisako et al. | 307/104 |
| 2011/0227666 A1* | 9/2011 | Manssen et al. | 333/32 |
| 2011/0273138 A1* | 11/2011 | Baarman et al. | 320/108 |
| 2012/0262000 A1* | 10/2012 | Urano | 307/104 |

FOREIGN PATENT DOCUMENTS

| | | | | |
|---|---|---|---|---|
| JP | 2004159456 A | * | 6/2004 | H02J 17/00 |
| JP | 2005-040342 | | 2/2005 | |
| JP | 2006-217731 | | 8/2006 | |
| JP | 2008-17941 A | | 1/2008 | |
| JP | 4080662 | | 2/2008 | |
| JP | 4089778 | | 3/2008 | |
| JP | 2008-263710 | | 10/2008 | |

OTHER PUBLICATIONS

Abstract of Japanese Patent Publication No. 2004-159456, dated Jun. 3, 2004.

International Search Report dated Jan. 19, 2010.

Extended Supplementary European Search Report from corresponding European Patent Application No. 09 82 7463.2, dated Sep. 16, 2013.

* cited by examiner

CAPSULE-TYPE MEDICAL DEVICE, POWER SUPPLY APPARATUS, AND POWER SUPPLY SYSTEM

CROSS REFERENCE TO RELATED APPLICATION

This application is a continuation application of PCT/JP2009/068423 filed on Oct. 27, 2009 and claims benefit of Japanese Applications No. 2008-294794 filed in Japan on Nov. 18, 2008 and No. 2008-297042 filed in Japan on Nov. 20, 2008, the entire contents of which are incorporated herein by this reference.

BACKGROUND OF INVENTION

1. Field of the Invention

The present invention relates to a capsule-type medical device that is introduced into a body of an individual to be examined and performs predetermined processing, a power supply apparatus that wirelessly supplies power to the capsule-type medical device from outside the body of the individual to be examined, and a power supply system that includes the capsule-type medical device and the power supply apparatus.

2. Description of the Related Art

A capsule-type endoscope that includes an image pickup function and a wireless function has appeared in the field of endoscopes. After being swallowed by an individual to be examined that is a subject for observation, the capsule-type endoscope travels through the inside of internal organs such as the stomach and small intestine along with the peristaltic movement thereof until being naturally excreted from the body of the individual to be examined. While travelling through the internal organs, the capsule-type endoscope sequentially picks up images of the inside of the internal organs using the image pickup function.

Image data that is picked up inside the individual to be examined by the capsule-type endoscope while travelling through the internal organs is sequentially transmitted to an external apparatus provided outside the subject by means of a wireless function such as wireless communication and stored in a memory. Because the individual to be examined carries the external apparatus including the wireless function and the memory function, the individual to be examined can carry out daily activities freely during the observation period from the time of swallowing the endoscope until excretion thereof. After picking up images, the images of the internal organs are displayed on a displaying section such as a display based on the image data stored in the memory of the external apparatus to thereby allow a physician to make a diagnosis.

A system that wirelessly supplies electric power to a capsule-type endoscope is disclosed, for example, in Japanese Patent No. 4080662. According to the aforementioned system, since a radio capsule (corresponds to a capsule-type endoscope) is kept inside an individual to be examined, electric power is supplied to inside the capsule-type endoscope by transmitting electric power into the capsule-type endoscope from the outside of the individual to be examined. According to this system, a power transmitting antenna is provided in an external apparatus, and a power receiving antenna is provided inside the capsule-type endoscope. The external apparatus supplies power into the capsule-type endoscope through the transmitting antenna and the receiving antenna to thereby enable observation operations of the capsule-type endoscope that is kept for an extended period of time inside the individual to be examined.

Further, a power supply apparatus disclosed in Japanese Patent No. 4089778 has a configuration in which electrical energy is induced in a power receiving coil of a capsule inside a body of an individual to be examined by a magnetic field that is generated by power transmission coils of three axes that are arranged in a wound manner on the body of the individual to be examined.

SUMMARY OF THE INVENTION

A capsule-type medical device according to an embodiment of the present invention receives an electric power from outside a body of an individual to be examined and performs predetermined processing inside the body, and includes: a processing circuit that performs the predetermined processing inside the body; and a power receiving circuit that has a power receiving coil that wirelessly receives an electric power from outside the body, a power receiving resonance capacitor, and an adjusting reactance section that is capable of adjusting a reactance that is connected to the power receiving coil and the power receiving resonance capacitor; wherein an impedance of the processing circuit and an impedance of the power receiving circuit are matched by adjusting a reactance of the adjusting reactance section.

A power supply apparatus according to another embodiment of the present invention wirelessly supplies an electric power from outside a body of an individual to be examined to a capsule-type medical device that performs predetermined processing inside the body of the individual to be examined, and includes: a power transmission coil that is disposed outside the body of the individual to be examined and that generates an AC magnetic field; a power transmitting resonance capacitor that is connected in series to the power transmission coil; and a power transmission coil drive section that drives the power transmission coil; wherein upon detecting a termination of a resonant state of the AC magnetic field, the power transmission coil drive section performs control that restores the AC magnetic field to a resonant state.

A power supply system according to a further embodiment of the present invention includes a capsule-type medical device and a power supply apparatus, in which the capsule-type medical device wirelessly receives an electric power from outside a body of an individual to be examined and performs predetermined processing inside the body, and the power supply apparatus wirelessly supplies an electric power from outside the body of the individual to be examined to the capsule-type medical device that is inside the body, wherein the capsule-type medical device includes: a processing circuit that performs the predetermined processing inside the body; and a power receiving circuit that is a resonant circuit with a predetermined resonance frequency that has a power receiving coil that receives an electric power from outside the body, a power receiving resonance capacitor, and an adjusting reactance section that is capable of adjusting a reactance that is connected to the power receiving coil and the power receiving resonance capacitor; wherein an impedance of the processing circuit and an impedance of the power receiving circuit are matched by adjusting a reactance of the adjusting reactance section; and the power supply apparatus includes: a power transmission coil that generates an AC magnetic field, a power transmitting resonance capacitor that is connected in series to the power transmission coil, and a power transmission coil drive section that drives the power transmission coil, wherein upon detecting a termination of a resonant state of the AC magnetic field by an abrupt fall in a driving current or an abrupt rise in a driving voltage, the power transmission coil drive section performs control that restores the AC magnetic field to a resonant state.

DETAILED DESCRIPTION OF THE PREFERRED EMBODIMENT(S)

First Embodiment

A power supply system 1 and a capsule-type endoscope 20 that is a capsule-type medical device according to a first embodiment of the present invention are described hereunder with reference to the drawings.

Figure 1:
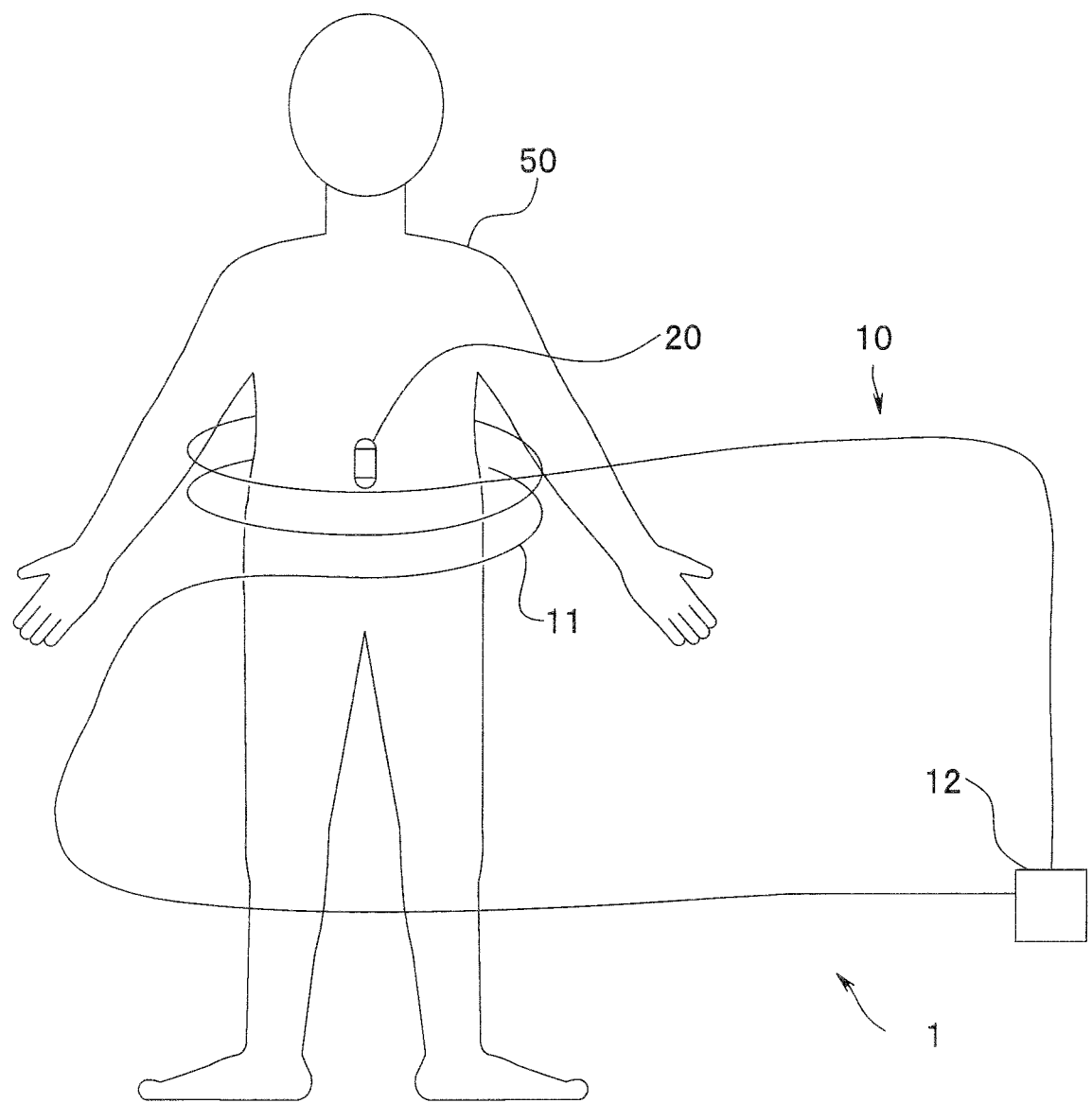
FIG. 1 is a schematic diagram that shows an overview of a power supply system including a capsule-type endoscope according to a first embodiment.

As shown in FIG. 1, a power supply system 1 of the present embodiment includes a capsule-type endoscope 20 (hereunder, also referred to as "endoscope") that, in a state in which the capsule-type endoscope 20 has been introduced into inside of an individual to be examined 50, wirelessly receives an electric power by electromagnetic induction from a power supply apparatus 10 that is arranged outside the individual to be examined 50. That is, according to the power supply apparatus 10, an alternating current is applied to a power transmission coil 11 from a power transmission circuit 12, and the power transmission coil 11 generates an AC magnetic field.

Figure 2:
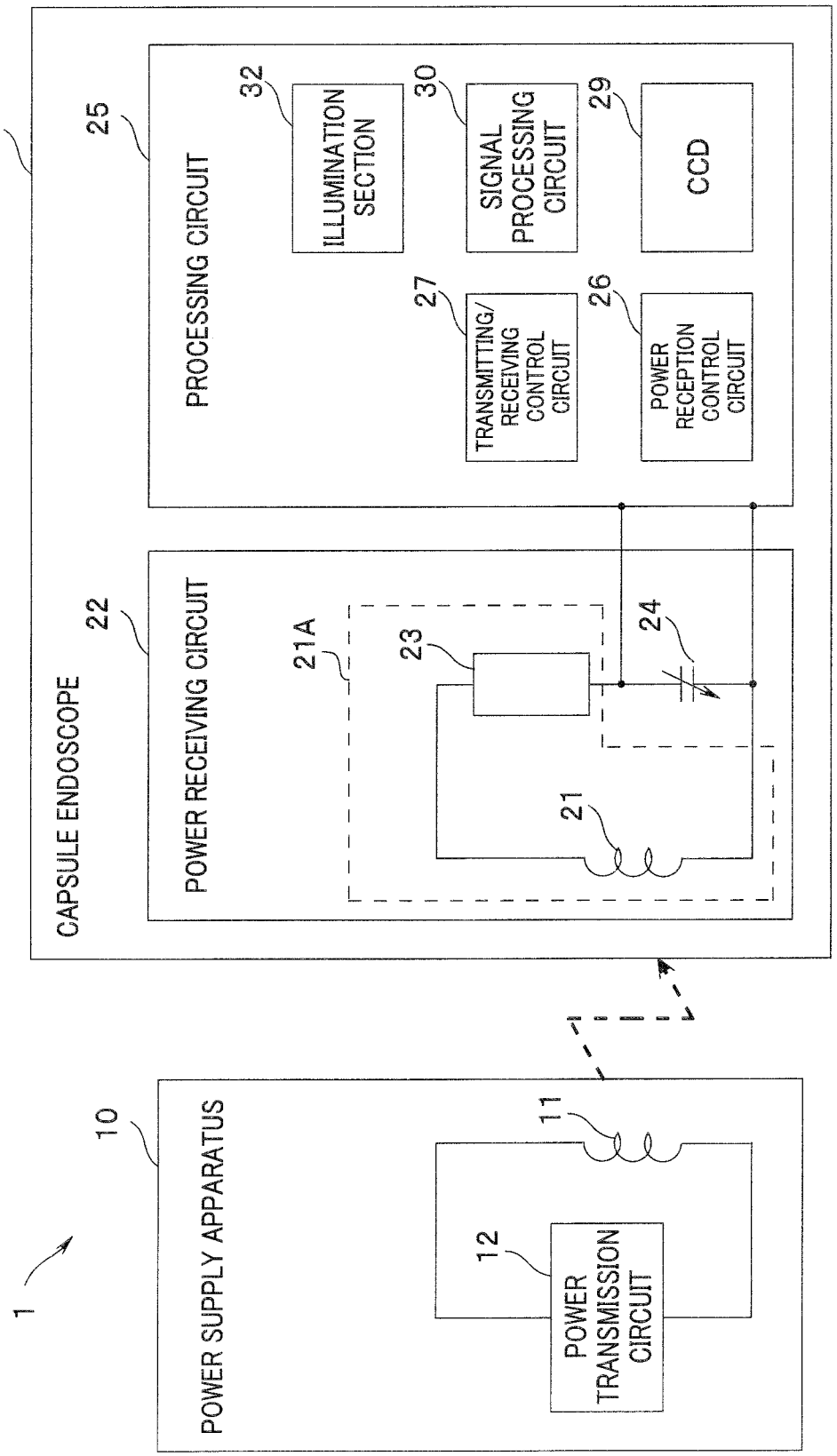
FIG. 2 is a configuration diagram of the power supply system including the capsule-type endoscope according to the first embodiment.

As shown in FIG. 2, the endoscope 20 has a power receiving circuit 22 that receives an electric power from the power supply apparatus 10, and a processing circuit 25 that performs a plurality of kinds of predetermined processing using the received electric power. The power receiving circuit 22 is a receiving resonant circuit with a predetermined resonance frequency that has a circuit 21A in which a power receiving coil 21 and an adjusting reactance section 23 that includes an adjusting reactance element are connected in series, and a power reception capacitor 24 for resonance that is connected to the processing circuit 25 in parallel with the circuit 21A.

Figure 3:
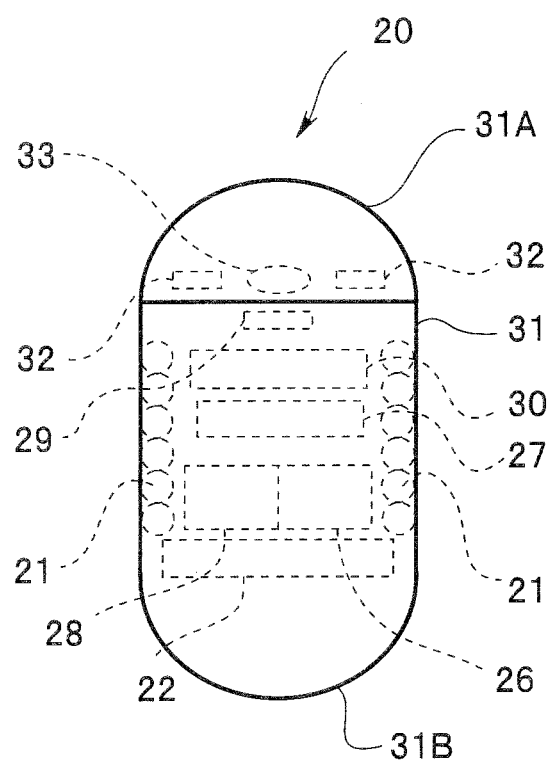
FIG. 3 is a cross-sectional schematic diagram for describing an overview of a structure of the capsule-type endoscope according to the first embodiment.

The power receiving coil 21 is a solenoid-type coil in which a conductive wire has been wound for a predetermined number of turns, and is arranged so that an axis of the coil is in a longitudinal direction of the capsule within a body portion of an elongated capsule-type case 31 (see FIG. 3). Here, the term "axis of the coil" refers to a central line of a magnetic path of the coil. In this connection, a configuration may be adopted in which the power receiving coil 21 is wound at one portion of the capsule-type case 31, the power receiving coil 21 may have a soft magnetic core therein, or the power receiving coil 21 may be wound on the outside of the capsule-type case 31.

The power reception capacitor 24 is a capacitor for making the resonance frequency of the power receiving circuit 22 and the frequency of a magnetic field that the power supply apparatus 10 generates approximately coincide, that is, match.

The processing circuit 25 includes a power reception control circuit 26, a transmitting/receiving control circuit 27, a CCD 29 that is an image pickup device, a signal processing circuit 30, and an illumination section 32.

More specifically, as shown in FIG. 3, the capsule-type medical device according to the present embodiment is the endoscope 20 that has the power receiving circuit 22 and the processing circuit 25 that are housed inside the elongated capsule-type case 31 that can be introduced into the body of the individual to be examined 50. The endoscope 20 is of a size that can be swallowed into the body from the mouth of the individual to be examined. The capsule-type case 31 is formed in a condition in which the inside thereof is sealed in a liquid-tight manner by elastically interfitting an approximately hemispherical distal end cover 31A that has transparency or translucency and a body portion cover 31B that is made of a colored material through which visible light cannot pass and in which one end portion is an approximately hemispherical cylindrical shape.

The endoscope 20 includes, within the capsule-type case 31, an illumination section 32 such as an LED that emits an illuminating light for illuminating an image-pickup site within a body cavity via the distal end cover 31A, a CCD 29 that receives a reflected light of the illuminating light to pick up an image of an image-pickup site within a body cavity, and an image-forming lens 33 that forms an image of an object on the CCD 29. In the endoscope 20, photographing is possible in the direction of a front end portion that is the distal end cover 31A side. The signal processing circuit 30 processes a picked-up image, and the transmitting/receiving control circuit 27 has a function that wirelessly transmits a picked-up image to outside of the body.

In the endoscope 20, for example, various control signals that are superimposed on the AC magnetic field that is a signal for supplying electric power are processed by the transmitting/receiving control circuit 27. A plurality of kinds of processing such as LED lighting processing by the illumination section 32, image pickup processing by the CCD 29, image processing by the signal processing circuit 30, and processing to transmit a picked-up image by the transmitting/receiving control circuit 27 are controlled based on the control signals.

In this case, a load of processing that the processing circuit 25 of the endoscope 20 performs differs according to the kind of the endoscope 20, in other words, according to the kind of processing that is performed. For example, a load of a processing circuit of a capsule-type endoscope that has a CCD that performs high-resolution color photographing is small in comparison to a capsule-type endoscope that performs only low-resolution black and white photographing. Further, even if capsule-type endoscopes have the same specifications, there are differences in the loads of the respective processing circuits 25 of individual products due to variations at the time of manufacture and the like. Consequently, there may be deviations with respect to the impedance of the power receiving circuit 22 and the impedance of the processing circuit 25.

As described above, unless the impedance of the processing circuit 25 that is the load and the impedance of the power receiving circuit 22 approximately coincide, that is, match, it is only possible to receive an amount of electric power that is less than the maximum electric power that, originally, can be received.

Figure 4:
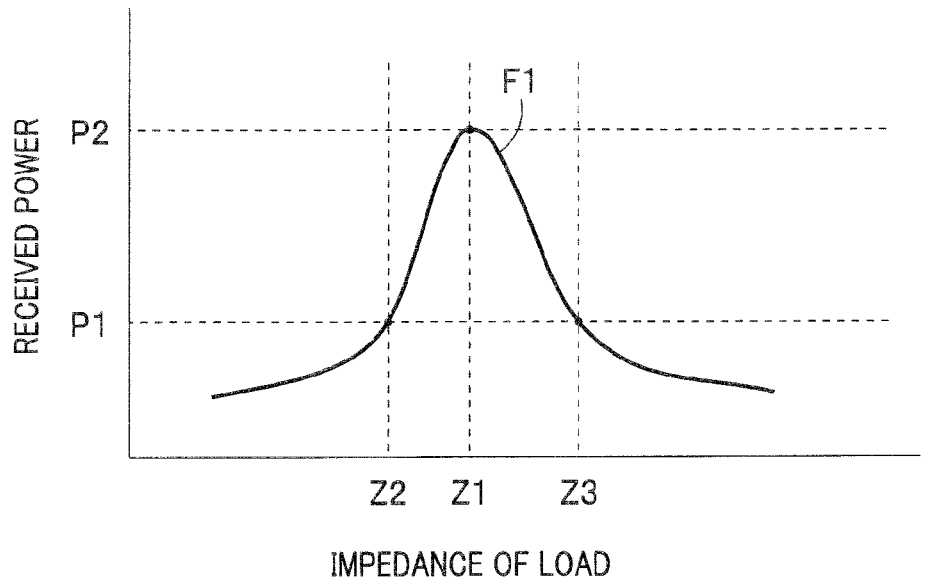
FIG. 4 is a view for describing a relationship between an impedance of a load and a received power.

In such a case, as shown in FIG. 4, when the impedance of the power receiving circuit 22 is represented by Z1, the relationship between the impedance of the load and the received power is as shown by the received power characteristics denoted by F1. Thus, the received power is a maximum P2 when the impedance of the processing circuit 25 that is the load is Z1. Further, if the impedance of the load deviates from Z1, as indicated by Z2 or Z3 in FIG. 4, the received power decreases to P1.

Figure 5:
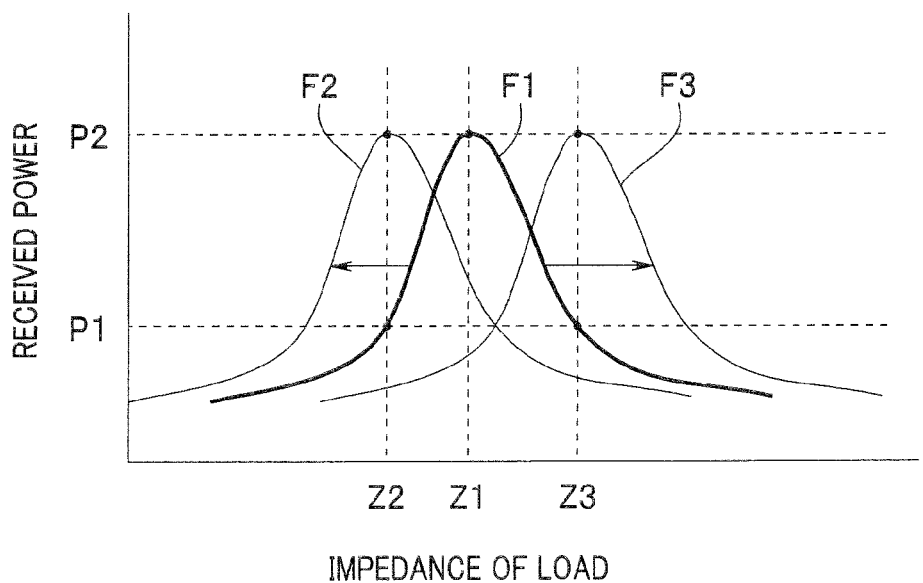
FIG. 5 is a view for describing a relationship between an impedance of a load and a received power.

However, according to the endoscope 20 of the present embodiment, since the power receiving circuit 22 has the adjusting reactance section 23, impedance matching can be performed between the power receiving circuit 22 and the processing circuit 25. More specifically, as shown in FIG. 5, when the load is large and the impedance is a small value of Z2, by using a capacitive adjusting reactance element the impedance of the power receiving circuit 22 can be adjusted to Z2 and the received power characteristics are as shown by F2. Similarly, when the load is small and the impedance is a large value of Z3, by using an inductive adjusting reactance element the impedance of the power receiving circuit 22 can be adjusted to Z3 and the received power characteristics are as shown by F3.

In this connection, it is also possible to adjust the impedance of the power receiving circuit 22 by means of the dimensions of the power receiving coil 21, the number of turns of a winding wire, or the presence or absence of a magnetic core as well as the characteristics thereof and the like. However, because of the particular use of the endoscope 20 that makes it necessary to house electronic components inside an extremely small space, there are restrictions such as the capacity of the power receiving coil 21, and thus it is not easy to adjust the aforementioned items.

Further, when using a capacitive adjusting reactance element, a value of the power reception capacitor 24 is adjusted in accordance with the capacitive adjusting reactance element that is connected.

According to the endoscope 20 of the present embodiment, for example, adjustment of the reactance of the adjusting reactance section 23 is performed at the time of manufacture.

Figure 6:
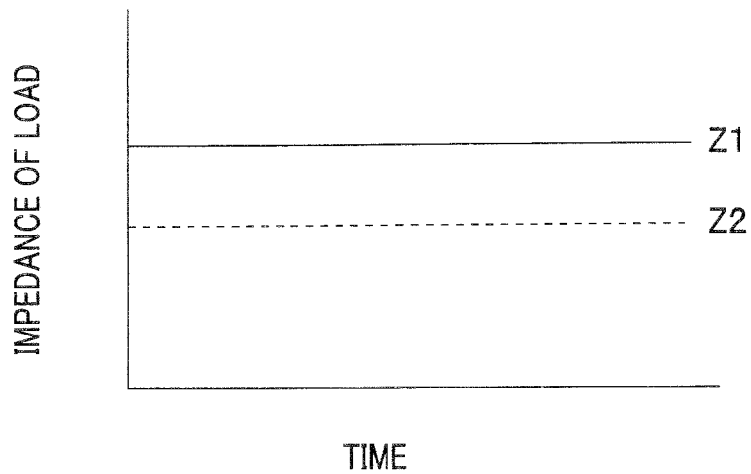
FIG. 6 is an explanatory drawing for describing a method of adjusting a reactance of an adjusting reactance element of the capsule-type endoscope according to the first embodiment.

As shown in FIG. 6, in a case of the endoscope 20 in which the impedance of the load is a constant value of Z2 over the passage of time, more specifically, with respect to driving of the respective kinds of processing of the processing circuit 25, the impedance of the power receiving circuit 22 is adjusted from Z1 to Z2 by the adjusting reactance section 23.

Figure 7:
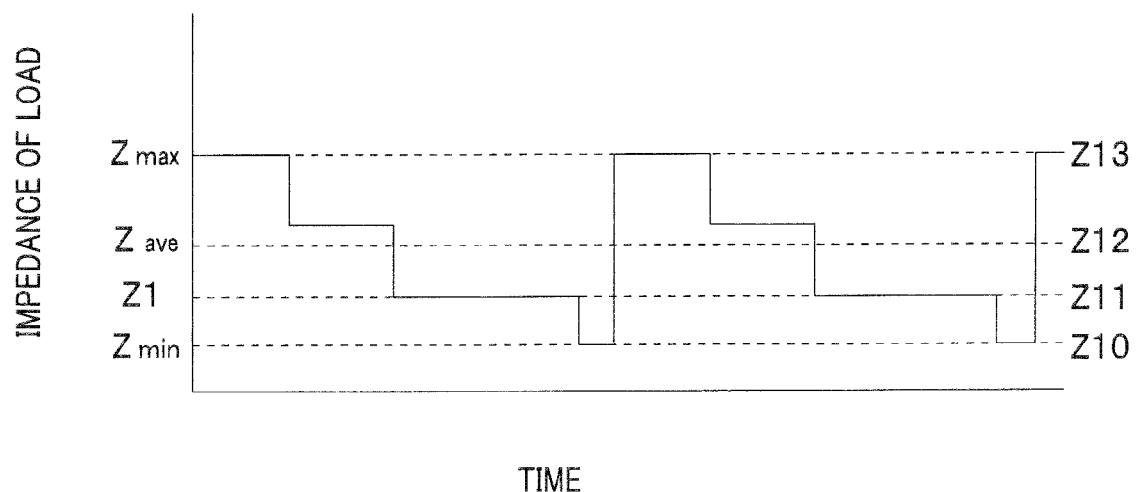
FIG. 7 is an explanatory drawing for describing a method of adjusting a reactance of the adjusting reactance element of the capsule-type endoscope of the first embodiment.

In contrast, as shown in FIG. 7, in a case of the endoscope 20 in which the impedance of the load changes over the passage of time, more specifically, with respect to driving of the respective kinds of processing of the processing circuit 25, the impedance of the power receiving circuit 22 is adjusted by the adjusting reactance section 23 by a method such as (A) matching the impedance to a state Z13 in which the impedance is largest, (B) matching the impedance to an average impedance Z12, (C) matching the impedance to an impedance Z11 at which the operating state is longest, or (D) matching the impedance to a state Z10 in which the impedance is smallest.

In this connection, in the endoscope 20, the adjusting reactance section 23 and the power reception capacitor 24 are constituted by a variable value device and the impedance is adjusted thereby.

As described above, since the impedance of the processing circuit 25 and the impedance of the power receiving circuit 22 are matched by adjusting or selecting the adjusting reactance section 23, the endoscope 20 can receive an electric power efficiently. More specifically, the efficiency with respect to transmitting and receiving electric power in the power supply system 1 is good.

Modification Example of First Embodiment

Hereunder, a power supply system 1A and an endoscope 20A of a modification example of the first embodiment of the present invention are described referring to the drawings. Since the capsule-type endoscope 20A of the modification example of the first embodiment is similar to the endoscope 20 of the first embodiment, like components are denoted by like reference symbols and a description of such components is omitted below.

Figure 8:
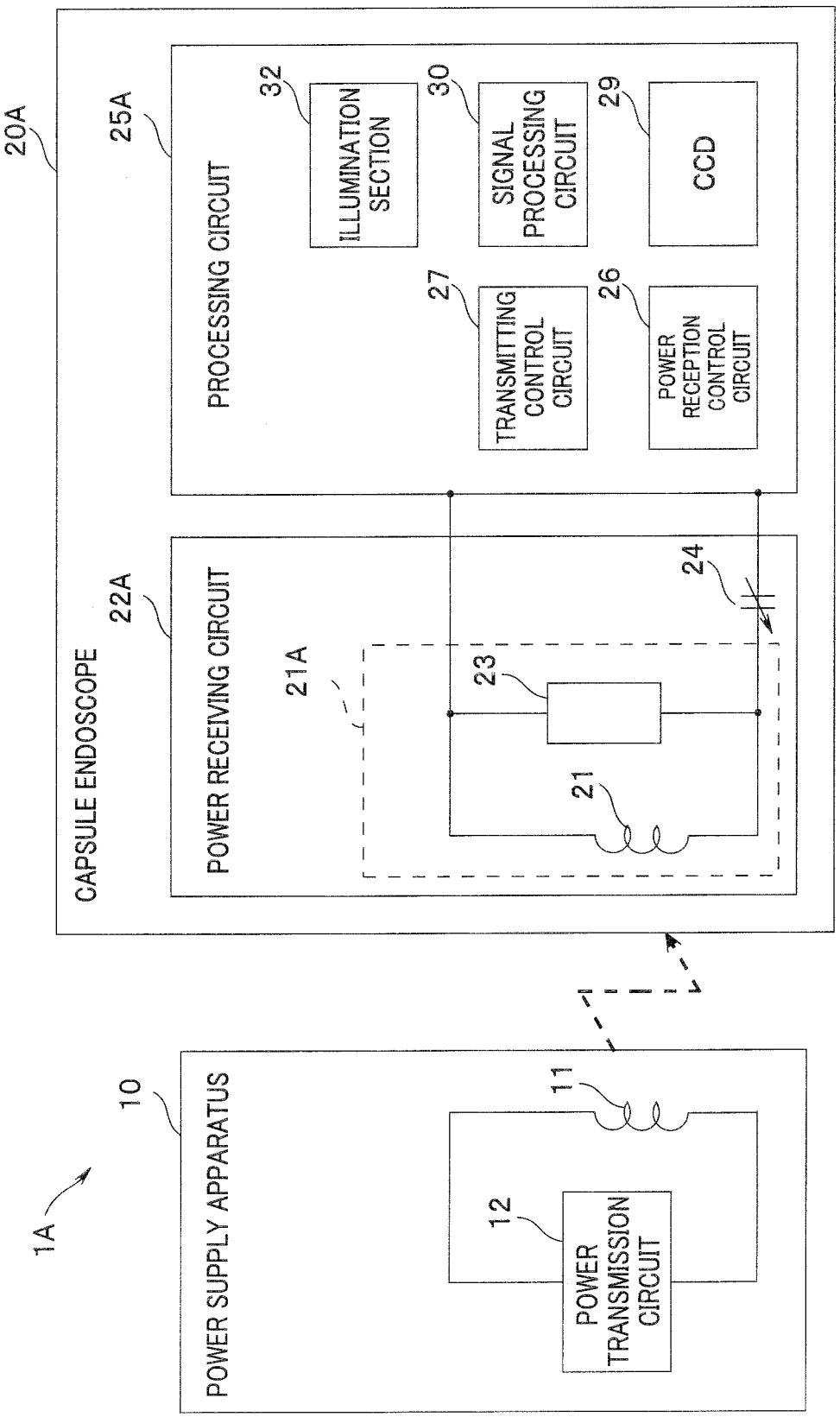
FIG. 8 is a configuration diagram of a power supply system including a capsule-type endoscope according to a modification example of the first embodiment.

As shown in FIG. 8, the endoscope 20A of the power supply system 1A of the present embodiment has the power receiving coil 21, the adjusting reactance section 23, and the power reception capacitor 24. The power receiving coil 21 and the adjusting reactance section 23 are connected in parallel, and the circuit 21A that has the power receiving coil 21 and the adjusting reactance section 23, and the power reception capacitor 24 are connected in series.

Since the endoscope 20A of the present modification example matches the impedance of a processing circuit 25A and the impedance of a power receiving circuit 22A by adjusting the reactance of the adjusting reactance section 23, the endoscope 20A can efficiently receive an electric power. More specifically, the efficiency with respect to transmitting and receiving electric power in the power supply system 1A is good.

Second Embodiment

Hereunder, a power supply system 1B and a capsule-type endoscope 20B that is a capsule-type medical device according to a second embodiment of the present invention are described referring to the drawings. Since the endoscope 20B of the second embodiment is similar to the endoscope 20 of the first embodiment, like components are denoted by like reference symbols and a description of such components is omitted below.

Figure 9:
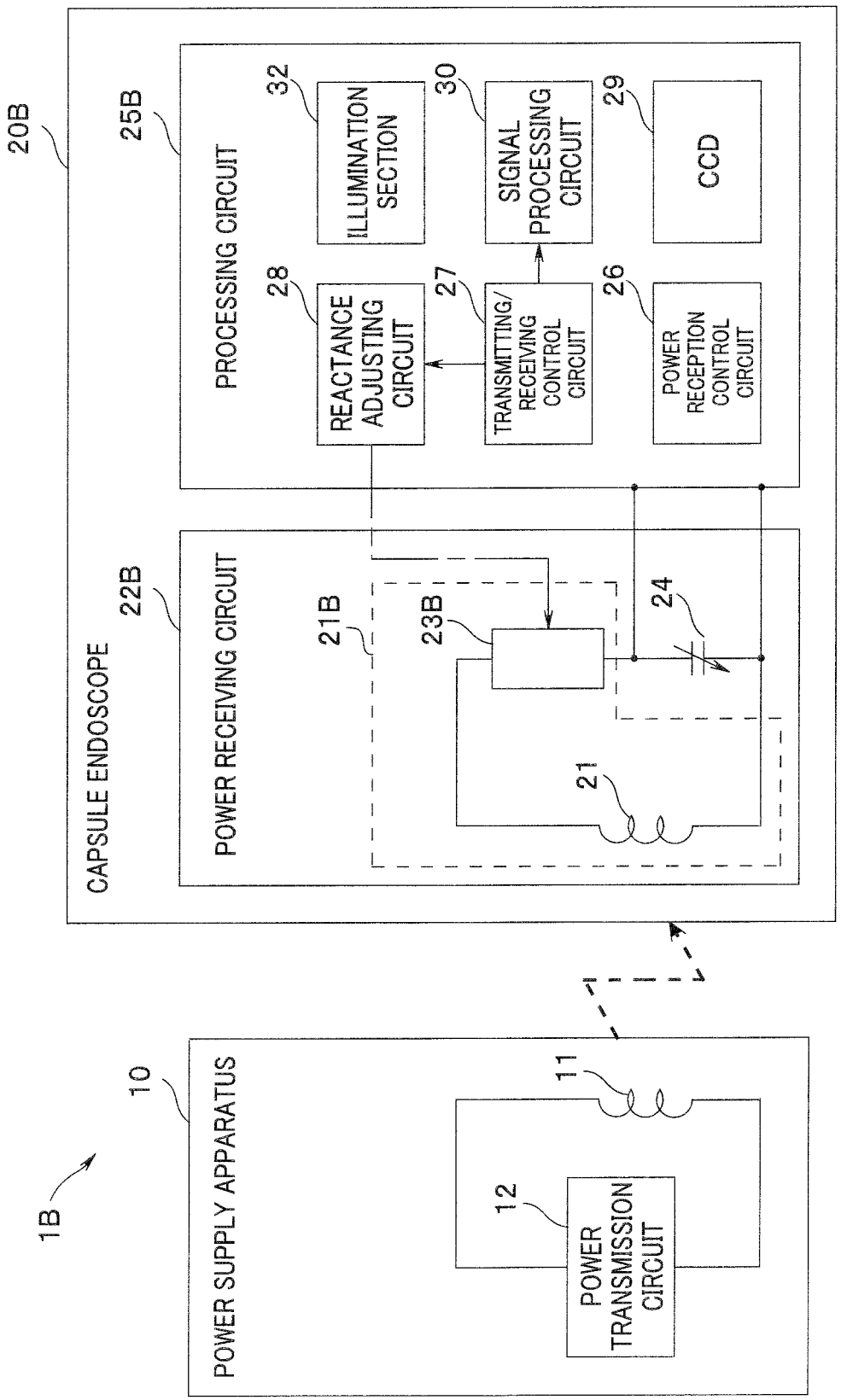
FIG. 9 is a configuration diagram of a power supply system including a capsule-type endoscope according to a second embodiment.

As shown in FIG. 9, the endoscope 20B of the present embodiment further includes an adjusting reactance section 23B and a reactance adjusting circuit 28. The reactance adjusting circuit 28 adjusts the reactance of the adjusting reactance section 23B based on a control signal that the transmitting/receiving control circuit 27 receives.

The respective loads of a plurality of predetermined kinds of processing that a processing circuit 25B of the endoscope 20B performs are different from each other. For example, since there is a large load and a small impedance with respect to LED lighting processing performed by the illumination section 32, the impedance of the processing circuit 25B changes between a time of lighting and a time of non-lighting. Consequently, the impedance of a power receiving circuit 22B and the impedance of the processing circuit 25B deviate with respect to each other. Various control signals that are superimposed on a signal for supplying electric power are processed by the transmitting/receiving control circuit 27, and a plurality of kinds of processing that the processing circuit 25B performs are controlled based on the control signals. The plurality of kinds of processing include, for example, LED lighting processing by the illumination section 32, image pickup processing by the CCD 29, image processing by the signal processing circuit 30, and processing to transmit a picked-up image by the transmitting/receiving control circuit 27.

According to the endoscope 20B, the reactance adjusting circuit 28 adjusts the reactance of the adjusting reactance section 23B in accordance with the respective kinds of processing that are performed based on the control signals received by the transmitting/receiving control circuit 27.

Figure 10:
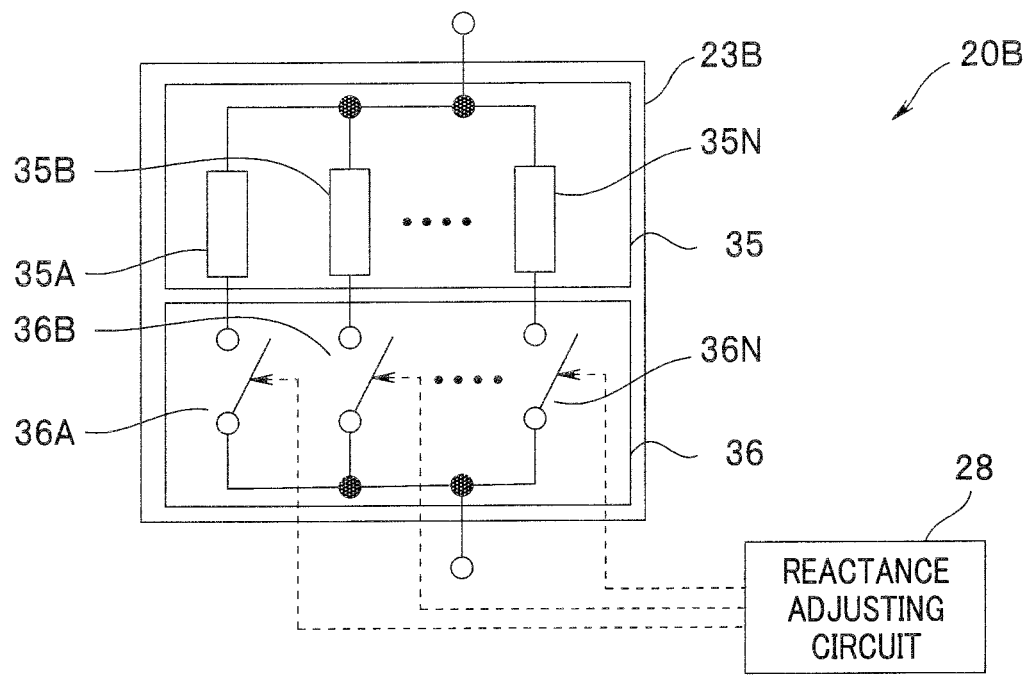
FIG. 10 is a schematic diagram for describing a structure of an adjusting reactance section of the capsule-type endoscope according to the second embodiment.

As shown in FIG. 10, the adjusting reactance section 23B has an adjusting reactance element group 35 including N reactance elements 35A to 35N that each has a different reactance and a reactance adjustment switch section 36 that has N switches 36A to 36N that switch a reactance element that is connected to the power receiving coil 21. In this connection, it is sufficient that the adjusting reactance section 23B has at least two reactance elements, or a configuration may be adopted that includes a variable reactance element that has a function that corresponds to a plurality of reactance elements that each has a different reactance.

The reactance elements 35A to 35N that match various kinds of processing that the processing circuit 25B performs are previously determined. Consequently, the adjusting reactance section 23B can adjust the reactance of the power receiving circuit 22B so as to match the impedance of various kinds of processing that the processing circuit 25B performs.

Figure 11:
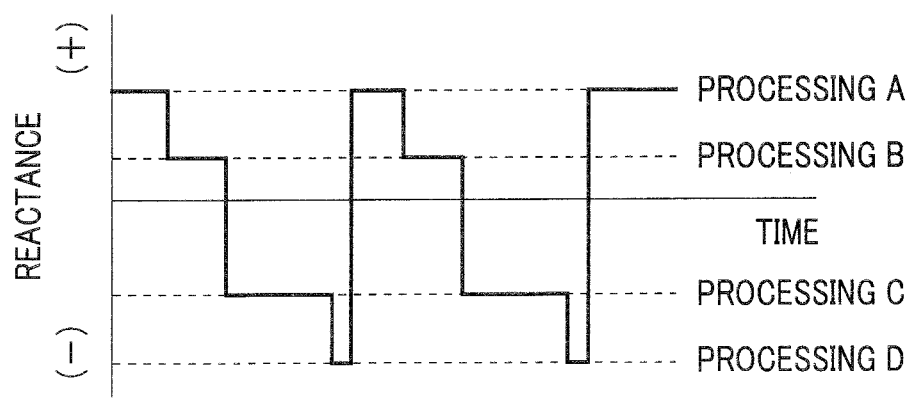
FIG. 11 is a schematic diagram for describing operations of the adjusting reactance section of the capsule-type endoscope according to the second embodiment.

For example, as shown in FIG. 11, when processing A is performed the adjusting reactance section 23B selects the reactance element 35A for which the reactance is a large positive value, when processing B is performed the reactance element 35B for which the reactance is a positive value is selected, when processing C is performed the reactance element 35C for which the reactance is a negative value is selected, and when processing D is performed the reactance element 35D for which the reactance is a large negative value is selected.

In addition to having the advantages of the endoscope 20 of the first embodiment, since the reactance adjusting circuit 28 adjusts a reactance of the adjusting reactance section 23B so as to match an impedance that is in accordance with processing of the processing circuit 25B and an impedance of the power receiving circuit 22B, the endoscope 20B of the present embodiment can efficiently receive an electric power. More specifically, the efficiency with respect to transmitting and receiving electric power in the power supply system 1B is good.

Particularly, since the reactance adjusting circuit 28 adjusts a reactance based on processing information that is received by the transmitting/receiving control circuit 27, the power supply system 1B has a simple configuration and it is difficult for a following delay to occur. More specifically, since a time from reception of a control signal for processing that is received by the transmitting/receiving control circuit 27 until the respective processing is actually performed is limited, and the reactance adjusting circuit 28 switches the reactance adjustment switch section 36 in that time period, the rate of change in the impedance of the processing circuit 25B can be followed.

In this connection, it is also possible to correspond to various reactances by means of a combined reactance value by connecting the adjusting reactance section 23B to a plurality of reactance elements at the same time.

Third Embodiment

Hereunder, a power supply system 1C and a capsule-type endoscope 20C that is a capsule-type medical device according to a third embodiment of the present invention are described referring to the drawings. Since the endoscope 20C of the third embodiment is similar to the endoscope 20B of the second embodiment, like components are denoted by like reference symbols and a description of such components is omitted below.

Figure 12:
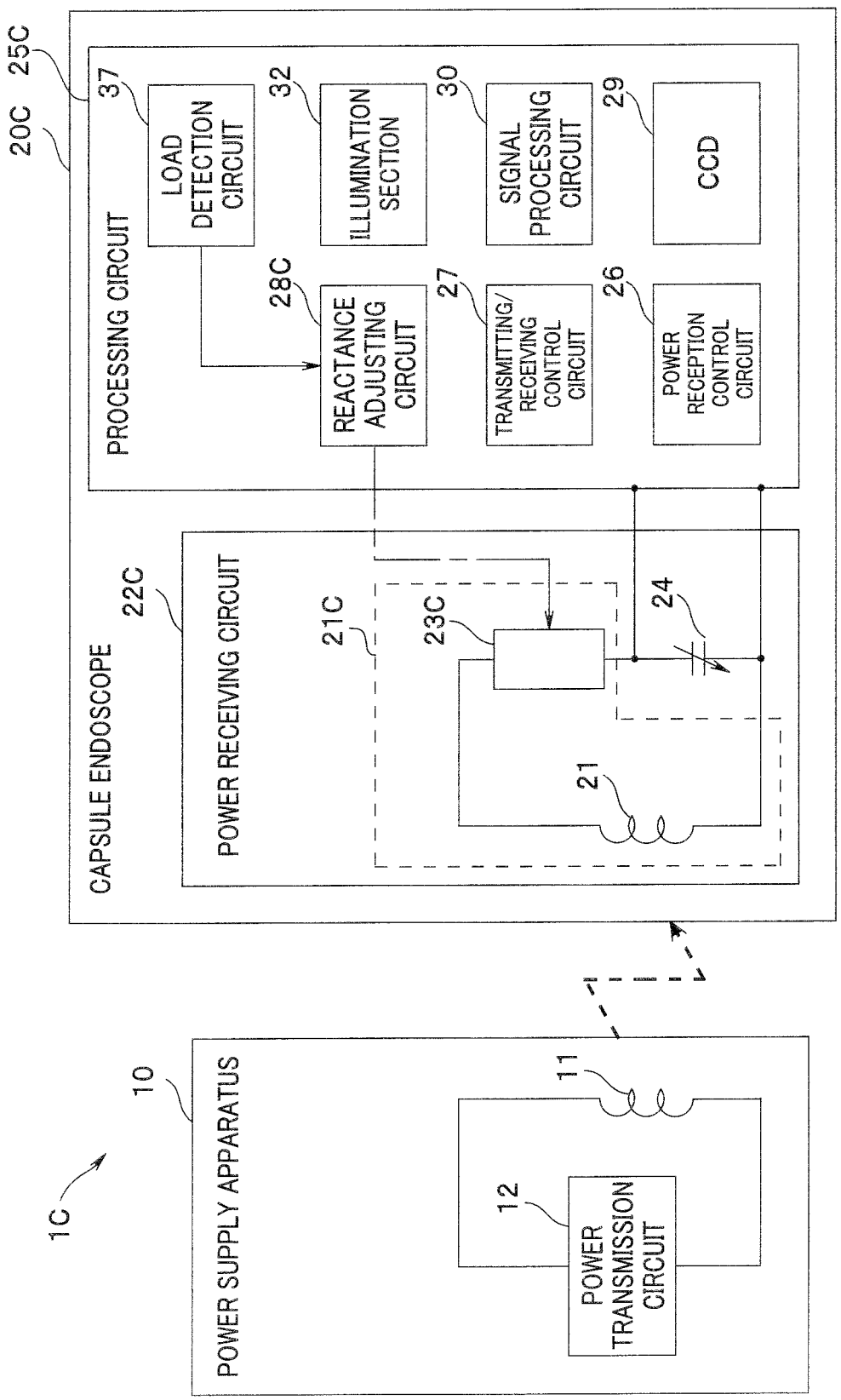
FIG. 12 is a configuration diagram of a power supply system including a capsule-type endoscope according to a third embodiment.

As shown in FIG. 12, the endoscope 20C of the power supply system 1C of the present embodiment further includes a load detection circuit 37. The load detection circuit 37 measures a load of a processing circuit 25C, in other words, an impedance, in real time. A reactance adjusting circuit 28C adjusts the reactance of a power receiving circuit 22C based on information of the load detection circuit 37. Note that the load detection circuit 37 may detect the impedance at predetermined intervals, and the reactance adjusting circuit 28C may also adjust the reactance at predetermined intervals.

In addition to having the advantages of the endoscope 20 of the first embodiment, since the reactance adjusting circuit 28C adjusts a reactance of an adjusting reactance section 23C so as to thereby match an impedance that is in accordance with processing of the processing circuit 25C and an impedance of the power receiving circuit 22C, the endoscope 20C of the present embodiment can efficiently receive an electric power. More specifically, the efficiency with respect to transmitting and receiving electric power in the power supply system 1C is good.

Particularly, since the reactance adjusting circuit 28C of the present embodiment adjusts a reactance based on an impedance of the processing circuit 25C that is detected by the load detection circuit 37, the accuracy is high.

Fourth Embodiment

A power supply system 1D and a power supply apparatus 10D of a fourth embodiment of the present invention are described hereunder with reference to the drawings.

Figure 13:
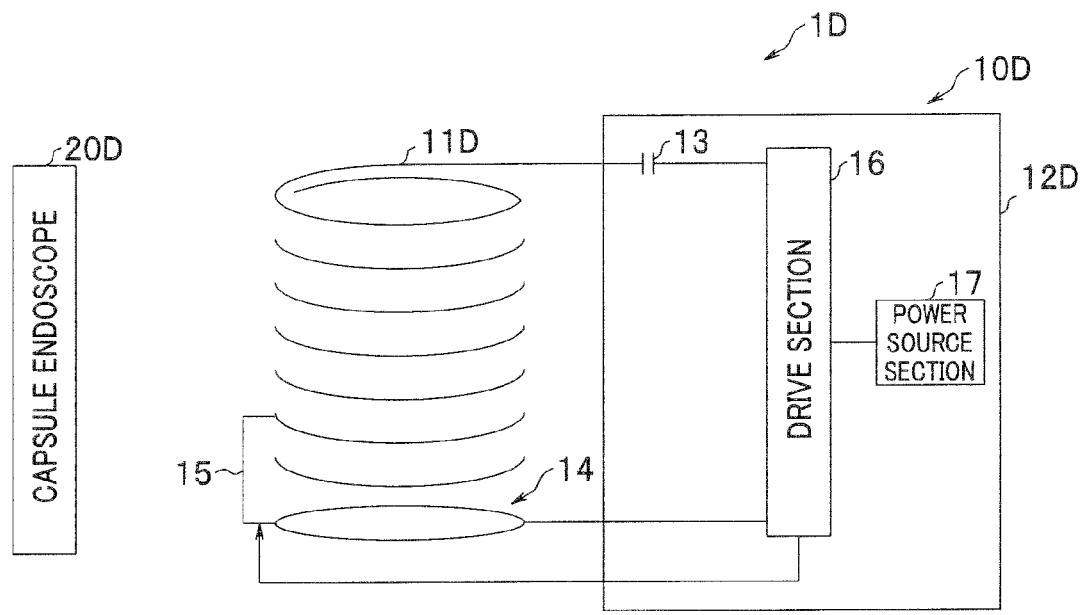
FIG. 13 is a configuration diagram that illustrates a configuration of principal parts of a power supply apparatus of an embodiment according to a fourth embodiment.

As shown in FIG. 13, the power supply system 1D of the present embodiment includes the power supply apparatus 10D that is disposed around the outside of the body of the individual to be examined 50, and a capsule-type endoscope 20D that is disposed inside the body of the individual to be examined. Unlike the endoscopes 20 to 20C described above, the endoscope 20D does not include an adjusting reactance section and the like.

As shown in FIG. 13, the power supply apparatus 10D has a power transmission coil 11D, a power transmitting resonance capacitor (hereunder, also referred to as "power transmission capacitor") 13 that is connected in series to one end side of the power transmission coil 11D, a coil length adjusting section 14 that is disposed on the other end side of the power transmission coil 11D, a conductor wire member 15 that electrically connects the power transmission coil 11D and the coil length adjusting section 14, a power transmission coil drive section (hereunder, also referred to as "drive section") 16 that drives the power transmission coil 11D, and a power source section 17 that supplies an electric power to the power transmission coil drive section 16.

In the power transmission coil 11D, the one end side is connected to the power transmission coil drive section 16 via the power transmission capacitor 13, and the other end side is connected to the power transmission coil drive section 16 via the conductor wire member 15 and the coil length adjusting section 14.

Although the coil length adjusting section 14 that is an electric conductor and the power transmission coil 11D are integrated and function as a variable inductance coil, the coil length adjusting section 14 and the power transmission coil 11D may be formed as separate bodies. For example, as shown in FIG. 13, one end side of the coil length adjusting section 14 has approximately the same diameter as the coil diameter of the power transmission coil 11D, and a central axis thereof is formed as a circular conductor wire that matches a central axis of the power transmission coil 11D. Further, the other end side of the coil length adjusting section 14 is connected to the power transmission coil drive section 16.

The conductor wire member 15 electrically connects the other end side of the power transmission coil 11D and the one end side of the coil length adjusting section 14. Further, the conductor wire member 15 is configured so as to be movable along a circular-shaped conductor wire on the one end side of the coil length adjusting section 14 and so that its own length is variable with respect to the length direction of the power transmission coil 11D in accordance with control of the power transmission coil drive section 16. More specifically, the conductor wire member 15 electrically connects the other end side of the power transmission coil 11D and the one end side of the coil length adjusting section 14 while forming a short-circuit therebetween.

The power transmission coil drive section 16 is connected to the power transmission capacitor 13 and the other end side of the coil length adjusting section 14. Upon detecting that a resonant state of a transmission resonant circuit that includes the power transmission coil 11D and the power transmission capacitor 13 has been terminated, the power transmission coil drive section 16 adjusts the coil length of the power transmission coil 11D by changing the short circuit position of the power transmission coil 11D by means of the conductor wire member 15.

More specifically, the inductance of a series circuit constituted by the power transmission coil drive section 16, the power transmission capacitor 13, the power transmission coil 11D, the conductor wire member 15, and the coil length adjusting section 14 is changed.

Next, the action of the power supply apparatus 10D is described. As described above, the power transmission coil 11D is disposed around the outside of the body of the individual to be examined 50, and the endoscope 20D is disposed inside the body of the individual to be examined. The endoscope 20D includes the power reception resonant circuit (power receiving circuit) 22 that includes the power receiving coil 21 that generates a current in accordance with an external magnetic field. Note that the resonance frequency of the transmission resonant circuit and the resonance frequency of the power reception resonant circuit 22 are set to be approximately the same frequency.

When the power source section 17 is turned on, an alternating current with a resonance frequency of a power transmission resonant circuit as a driving current for driving the power transmission coil 11D is outputted from the power transmission coil drive section 16. Thereupon, an AC magnetic field of a frequency that matches the resonance frequency of the power reception resonant circuit 22 of the endoscope 20D is generated from the power supply apparatus 10.

The power transmission coil drive section 16 monitors a current or a voltage that is being supplied to the power transmission coil 11D. More specifically, in a case where the power transmission coil drive section 16 performs constant-voltage driving, the power transmission coil drive section 16 monitors the driving current, and in a case where the power transmission coil drive section 16 performs constant-current driving, the power transmission coil drive section 16 monitors the driving voltage.

In this case, if the inductance of the power transmission coil 11D changes as a result of a change in the shape of the power transmission coil 11D due to a change in the posture of the individual to be examined or the like, a resonant state of the transmission resonant circuit is terminated. More specifically, the power transmission coil drive section 16 continues to apply a driving current with the resonance frequency of the transmission resonant circuit that corresponds to the time before the shape of power transmission coil 11D changed, to the power transmission coil 11D. Consequently, the power supply apparatus 10D can no longer generate a magnetic field efficiently.

The power transmission coil drive section 16 of the power supply apparatus 10D detects a termination of a resonant state of the transmission resonant circuit by an abrupt fall in a driving current or an abrupt rise in a driving voltage that is being supplied to the power transmission coil 11D. Upon detecting a termination of the resonant state, the power transmission coil drive section 16 performs control that changes the short circuit position of the power transmission coil 11D by means of the conductor wire member 15 in order to restore the transmission resonant circuit to a resonant state.

In response to the control of the power transmission coil drive section 16, the conductor wire member 15 changes its own length while moving along the circular-shaped conductor wire on the one end side of the coil length adjusting section 14.

While changing the short circuit position of the power transmission coil 11D by means of the conductor wire member 15, the power transmission coil drive section 16 monitors a driving current or a driving voltage that is being supplied to the power transmission coil 11D. Based on a monitoring result, when the power transmission coil drive section 16 detects that the driving current or the driving voltage has returned to the former state, the power transmission coil drive section 16 performs control to fix the short circuit position of the power transmission coil 11D by means of the conductor wire member 15.

By means of the above described control performed by the power transmission coil drive section 16, the coil length of the power transmission coil 11D is adjusted so that the inductance becomes a level that enables restoration of a resonant state of the transmission resonant circuit, and a magnetic field that is based on resonance driving at the predetermined resonance frequency as described above is generated from the power supply apparatus 10D.

In this connection, the power transmission coil drive section 16 may be configured so as to detect a termination of a resonant state of the transmission resonant circuit by, for example, detecting a change in a magnetic field intensity that the power transmission coil 11D is actually generating, using an unshown magnetic field sensor. Further, the power transmission coil drive section 16 may be configured so as to detect that a termination of a resonant state by, for example, detecting a change in the inductance of the power transmission coil 11D that is obtained using an unshown LC meter.

As described in the foregoing, even when a resonant state has been terminated, the power supply apparatus 10D of the present embodiment can promptly restore the resonant state by adjusting the inductance of the power transmission coil 11D. More specifically, in the power supply system 1D and the power supply apparatus 10D of the present embodiment, the efficiency with respect to wirelessly transmitting and receiving electric power is good.

Fifth Embodiment

Hereunder, a power supply system 1E and a power supply apparatus 10E according to a fifth embodiment of the present invention are described. Since the power supply system 1E and the power supply apparatus 10E are similar to the power supply system 1D and the power supply apparatus 10D of the fourth embodiment, like components are denoted by like reference symbols and a description of such components is omitted below.

Figure 14:
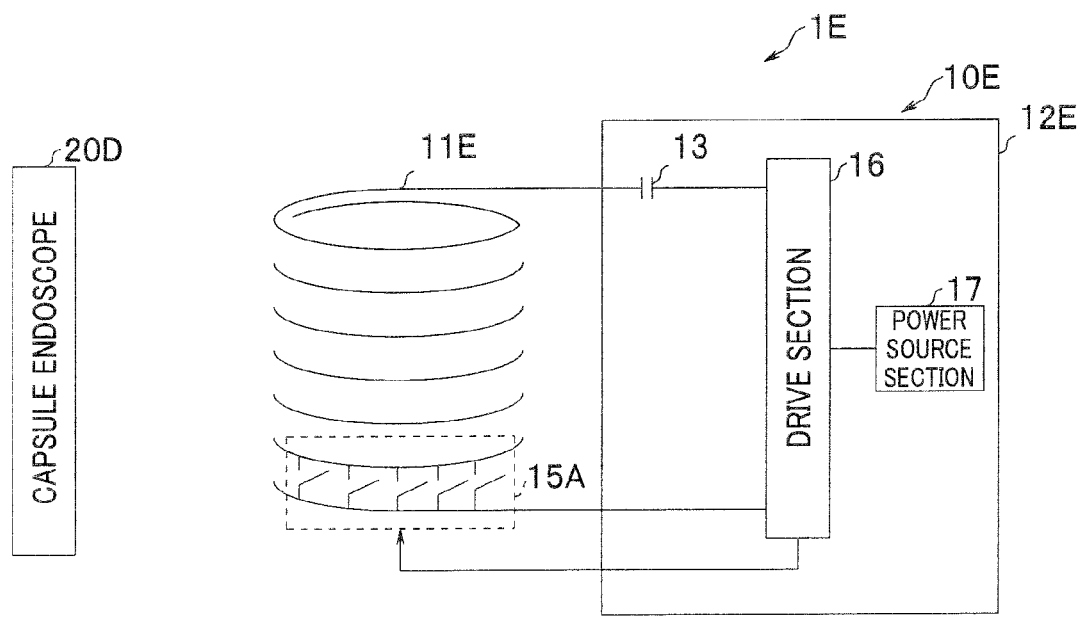
FIG. 14 is a configuration diagram that illustrates a configuration of principal parts of a power supply apparatus according to a fifth embodiment.

As shown in FIG. 14, the power supply apparatus 10E has a power transmission coil 11E, the power transmission capacitor 13 that is connected in series to one end side of the power transmission coil 11E, a switch group 15A that is disposed on the other end side of the power transmission coil 11E, a power transmission coil drive section 16 that drives the power transmission coil 11E, and a power source section 17 that supplies power to the power transmission coil drive section 16.

The one end side of the power transmission coil 11E is connected to the power transmission coil drive section 16 via the power transmission capacitor 13, and the other end side thereof is directly connected to the power transmission coil drive section 16.

As shown in FIG. 14, the switch group 15A is composed by a plurality of switches that can electrically connect a conductor wire of an endmost portion of the other end side of the power transmission coil 11E and a conductor wire on an inner side that is one turn of wire away from the endmost portion. Further, the switch group 15A is configured such that each switch can be switched on or off in accordance with the control of the power transmission coil drive section 16.

Upon detecting a termination of a resonant state of the transmission resonant circuit, in order to restore the resonant state, the power transmission coil drive section 16 of the power supply apparatus 10E performs control to switch on any one switch among the switches of the switch group 15A.

The power transmission coil drive section 16 monitors a driving current or a driving voltage that is being supplied to the power transmission coil 11E, while switching a switch that is switched on among the switch group 15A in sequential order. Subsequently, based on a monitoring result, when the power transmission coil drive section 16 detects that the driving current or the driving voltage has returned to a previous state, the power transmission coil drive section 16 performs control to fix an on/off state of each switch of the switch group 15A.

By means of the above described control performed by the power transmission coil drive section 16, the coil length of the power transmission coil 11E is adjusted so that the inductance thereof becomes a level that enables restoration of a resonant state of the transmission resonant circuit, and a magnetic field of a predetermined resonant state is generated from the power supply apparatus 10E.

As described in the foregoing, even when a resonant state has been terminated, the power supply system 1E and the power supply apparatus 10E of the present embodiment can promptly restore the resonant state by appropriately adjusting the inductance of the power transmission coil 11E. More specifically, in the power supply system 1E and the power supply apparatus 10E of the present embodiment, the efficiency with respect to transmitting and receiving electric power is good.

Sixth Embodiment

Hereunder, a power supply system 1F and a power supply apparatus 10F according to a sixth embodiment of the present invention are described. Since the power supply system 1F and the power supply apparatus 10F are similar to the power supply system 1D and the power supply apparatus 10D of the fourth embodiment, like components are denoted by like reference symbols and a description of such components is omitted below.

Figure 15:
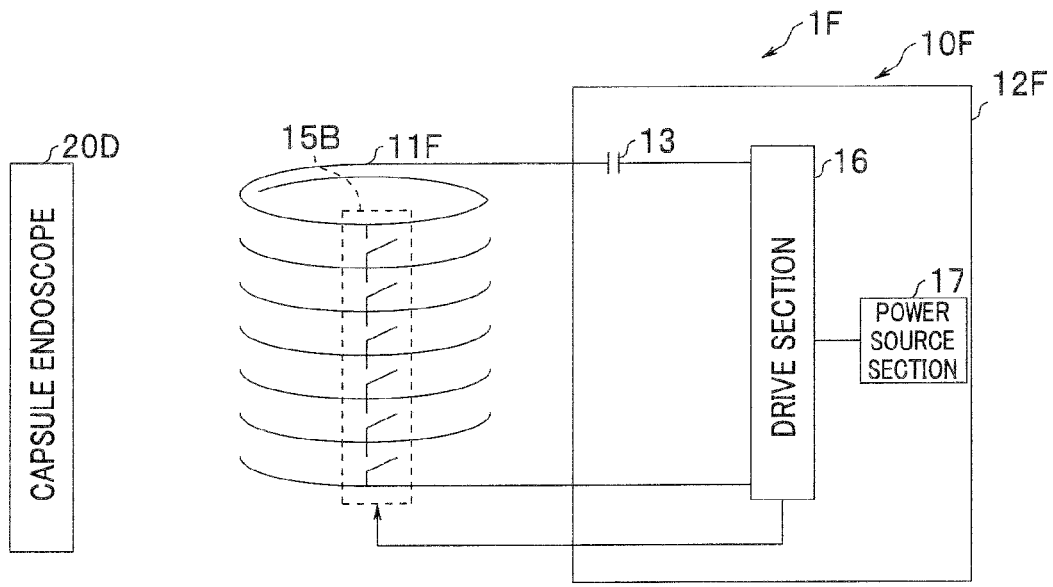
FIG. 15 is a configuration diagram that illustrates a configuration of principal parts of a power supply apparatus according to a sixth embodiment.

As shown in FIG. 15, the power supply apparatus 10F has a power transmission coil 11F that is disposed around the outside of a body of an individual to be examined, the power transmission capacitor 13 for resonance that is serially connected to one end side of the power transmission coil 11F, a switch group 15B that can electrically connect together conductor wires that constitute the power transmission coil 11F, the power transmission coil drive section 16 that drives the power transmission coil 11F, and the power source section 17 that supplies power to the power transmission coil drive section 16.

The one end side of the power transmission coil 11F is connected to the power transmission coil drive section 16 via the power transmission capacitor 13, and the other end side thereof is directly connected to the power transmission coil drive section 16.

As shown in FIG. 15, the switch group 15B is composed by a plurality of switches of the same or approximately the same number as the number of turns of the power transmission coil 11F. The plurality of switches are provided over an area from the one end side to the other end side of the power transmission coil 11F. The switch group 15B is configured such that each switch can be switched on or off in accordance with the control of the power transmission coil drive section 16.

When the power transmission coil drive section 16 of the power supply apparatus 10F detects a termination of a resonant state of the transmission resonant circuit, in order to restore the resonant state, the power transmission coil drive section 16 performs control to switch on at least any one switch among the switches included in the switch group 15B.

The power transmission coil drive section 16 monitors a driving current or a driving voltage while switching a switch that is switched on in the switch group 15B in sequential order. Subsequently, based on a monitoring result, when the power transmission coil drive section 16 detects that the driving current or the driving voltage has returned to a previous state, the power transmission coil drive section 16 performs control to fix an on/off state of each switch of the switch group 15B.

By means of the above described control performed by the power transmission coil drive section 16, the coil length of the power transmission coil 11F is adjusted so that the inductance thereof becomes a level that enables restoration of the resonant state of the transmission resonant circuit, and a magnetic field of a predetermined resonant state is generated from the power supply apparatus 10F.

As described in the foregoing, even when a resonant state has been terminated, the power supply system 1F and the power supply apparatus 10F of the present embodiment can promptly restore the resonant state by appropriately adjusting the inductance of the power transmission coil 11F. More specifically, in the power supply system 1F and the power supply apparatus 10F of the present embodiment, the efficiency with respect to transmitting and receiving electric power is good.

Further, for example, by switching an on/off state of each switch of the switch group 15B according to a predetermined pattern, such as alternately, the power supply apparatus 10F can adjust the inductance of the power transmission coil 11F without narrowing a power supply range.

Seventh Embodiment

Hereunder, a power supply system 1G and a power supply apparatus 10G according to a seventh embodiment of the present invention are described. Since the power supply system 1G and the power supply apparatus 10G are similar to the power supply system 1D and the power supply apparatus 10D of the fourth embodiment, like components are denoted by like reference symbols and a description of such components is omitted below.

Figure 16:
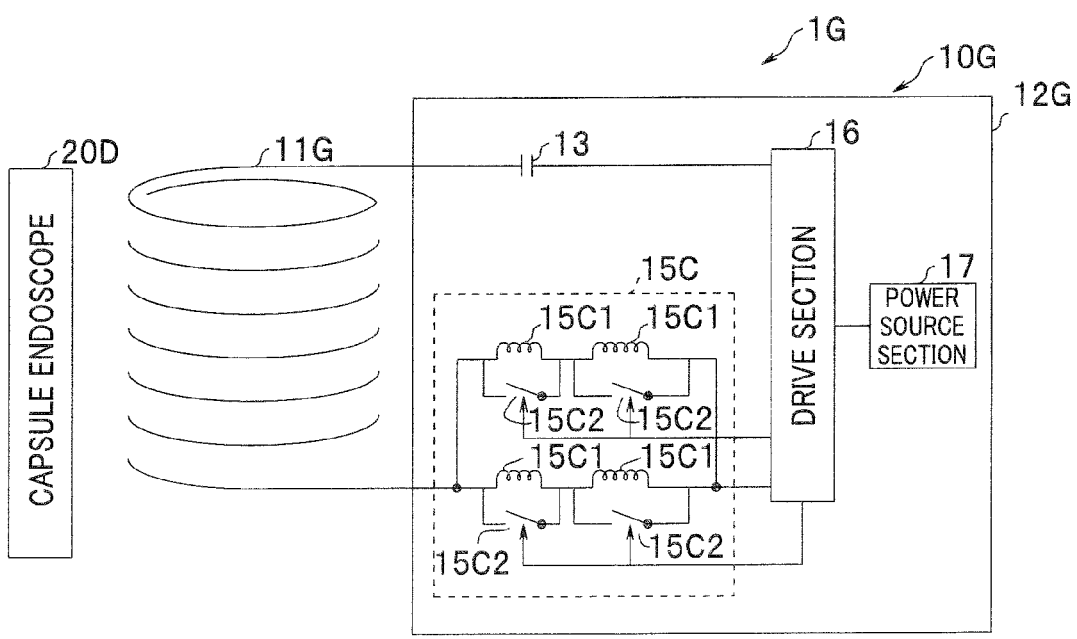
FIG. 16 is a configuration diagram that illustrates a configuration of principal parts of a power supply apparatus according to a seventh embodiment.

As shown in FIG. 16, the power supply apparatus 10G has a power transmission coil 11G, the power transmission capacitor 13 that is connected in series to one end side of the power transmission coil 11G, a power transmitting inductance adjustment section 15C that is connected to another end side of the power transmission coil 11G, the power transmission coil drive section 16 that drives the power transmission coil 11G, and the power source section 17 that supplies power to the power transmission coil drive section 16.

The one end side of the power transmission coil 11G is connected to the power transmission coil drive section 16 via the power transmission capacitor 13, and the other end side thereof is connected to the power transmission coil drive section 16 via the power transmitting inductance adjustment section 15C.

As shown in FIG. 16, the power transmitting inductance adjustment section 15C has a configuration in which a plurality of auxiliary coils 15C1 are connected in a series-parallel arrangement. Further, switches 15C2 for switching an electrical conduction state of the respective auxiliary coils 15C1 are connected in parallel to the plurality of auxiliary coils 15C1, respectively.

When the power transmission coil drive section 16 of the power supply apparatus 10G detects a termination of a resonant state of the transmission resonant circuit, in order to restore the resonant state, the power transmission coil drive section 16 performs control to switch off at least any one switch of the respective switches 15C2.

Meanwhile, at the power transmitting inductance adjustment section 15C, a current flows to the auxiliary coil 15C1 corresponding to the switch 15C2 that is switched off.

The power transmission coil drive section 16 monitors a driving current or a driving voltage while switching a switch that is switched off among the switches 15C2 in sequential order. Subsequently, based on a monitoring result, when the power transmission coil drive section 16 detects that the driving current or the driving voltage has returned to a previous state, the power transmission coil drive section 16 performs control to fix an on/off state of the respective switches 15C2.

By means of the above described control performed by the power transmission coil drive section 16, an adjustment for making the inductance a level that enables restoration of a resonant state of the power transmission resonant circuit is performed at the power transmitting inductance adjustment section 15C, and a magnetic field of a predetermined resonant state as described above is generated from the power supply apparatus 10G.

As described in the foregoing, even when a resonant state has been terminated, the power supply system 1F and the power supply apparatus 10F of the present embodiment can promptly restore the resonant state by appropriately adjusting the inductance of the power transmitting inductance adjustment section 15C according to the amount of change in the inductance of the power transmission coil 11G. More specifically, in the power supply system 1G and the power supply apparatus 10G of the present embodiment, the efficiency with respect to transmitting and receiving electric power is good.

Eighth Embodiment

Hereunder, a power supply system 1H and a power supply apparatus 10H according to an eighth embodiment of the present invention are described. Since the power supply system 1H and the power supply apparatus 10H are similar to the power supply system 1D and the power supply apparatus 10D of the fourth embodiment, like components are denoted by like reference symbols and a description of such components is omitted below.

Figure 17:
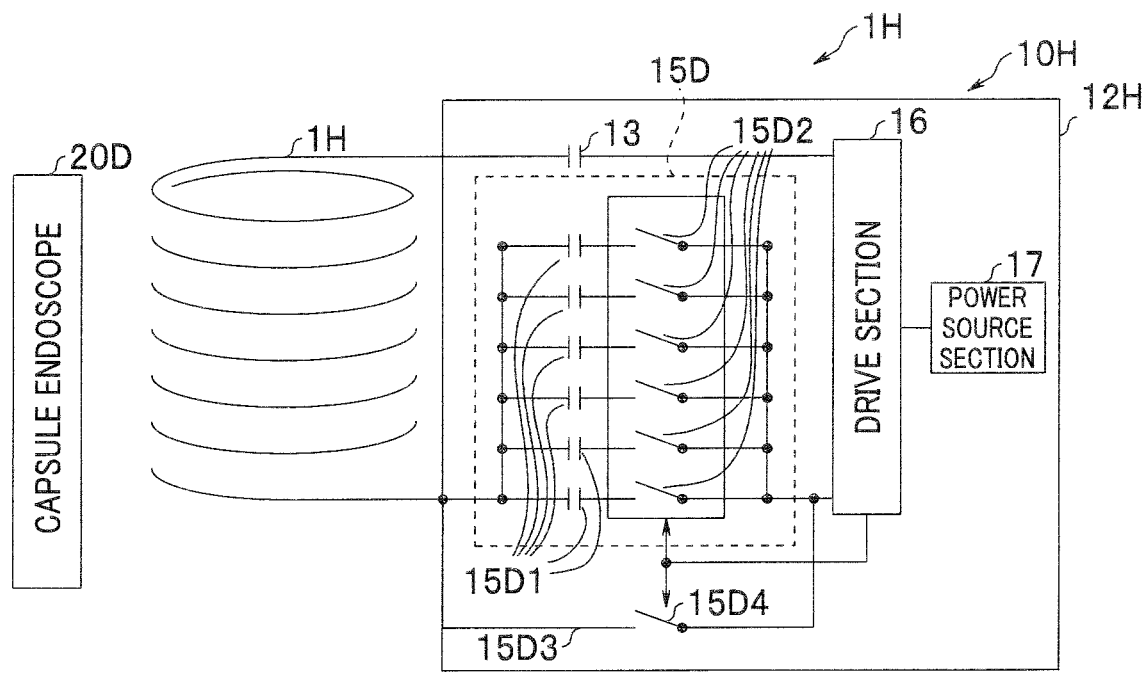
FIG. 17 is a configuration diagram that illustrates a configuration of principal parts of a power supply apparatus according to an eight embodiment.

As shown in FIG. 17, the power supply apparatus 10H has a power transmission coil 11H that is disposed around the outside of a body of an individual to be examined, the power transmission capacitor 13 that is connected in series to one end side of the power transmission coil 11H, a capacitance adjustment section 15D that is connected to the other end side of the power transmission coil 11H, a bypass line 15D3 that is connected to the other end side of the power transmission coil 11H, the power transmission coil drive section 16 that drives the power transmission coil 11H, and the power source section 17 that supplies power to the power transmission coil drive section 16.

The one end side of the power transmission coil 11H is connected to the power transmission coil drive section 16 via the power transmission capacitor 13, and the other end side thereof is connected to the power transmission coil drive section 16 via the capacitance adjustment section 15D and the bypass line 15D3.

As shown in FIG. 17, the capacitance adjustment section 15D is provided between the other end side of the power transmission coil 11H and the power transmission coil drive section 16, and has a configuration in which a plurality of auxiliary capacitors 15D1 are connected in parallel. Further, switches 15D2 for switching an electrical conduction state of the respective auxiliary capacitors 15D1 are connected in parallel to the plurality of auxiliary coils 15C1, respectively.

The bypass line 15D3 connects the other end side of the power transmission coil 11H and the power transmission coil drive section 16 while bypassing the capacitance adjustment section 15D. A switch 15D4 provided partway along the bypass line 15D3 has a configuration that allows the switch 15D4 to be switched on or off according to the control of the power transmission coil drive section 16.

Next, the action of the power supply apparatus 10H is described. In this connection, in an initial state, by switching all of the switches 15D2 off, a current does not flow to any of the plurality of auxiliary capacitors 15D1, and further, by switching the switch 15D4 on, a current flows to the bypass line 15D3.

When the power transmission coil drive section 16 of the power supply apparatus 10H detects a termination of a resonant state of the power transmission resonant circuit, in order to restore the resonant state, the power transmission coil drive section 16 performs control to switch off the switch 15D4 and switch on at least any one switch among the respective switches 15D2.

In this case, in the capacitance adjustment section 15D, a current flows to the auxiliary capacitor 15D1 that corresponds to the switch 15D2 that is switched on. While switching a switch that is switched on among the respective switches 15D2 in sequential order while keeping the switch 15D4 in an off state, the power transmission coil drive section 16 monitors a driving current or a driving voltage that is being supplied to the power transmission coil 11H. Subsequently, based on a monitoring result, when the power transmission coil drive section 16 detects that the driving current or the driving voltage has returned to a previous state, the power transmission coil drive section 16 performs control to fix the switch 15D4 in an off state and also fix an on/off state of the respective switches 15D2.

By means of the above described control performed by the power transmission coil drive section 16, an adjustment for making a capacitance a level that enables restoration of a resonant state of the power transmission resonant circuit is performed at the capacitance adjustment section 15D, and a magnetic field of a predetermined resonant state as described above is generated from the power supply apparatus 10H.

In this connection, in the power supply apparatus 10H, by setting the capacitance of the respective auxiliary capacitors 15D1 of the capacitance adjustment section 15D in a geometrically progressive fashion using a common ratio of 1/2 such as, for example, in the manner C, C/2, C/4, C/8, . . . , the total number of the auxiliary capacitors 15D1 and/or the switches 15D2 included in the capacitance adjustment section 15D can be reduced. Further, a variable capacitance capacitor may be used as the capacitance adjustment section 15D, or a variable capacitance capacitor that has a function of the capacitance adjustment section 15D may be used as the power transmitting resonance capacitor 13.

As described in the foregoing, even when a resonant state has been terminated, the power supply system 1H and the power supply apparatus 10H of the present embodiment can promptly restore the resonant state by appropriately adjusting the capacitance of the capacitance adjustment section 15D according to the amount of change in the inductance of the power transmission coil 11H. More specifically, in the power supply system 1H and the power supply apparatus 10H of the present embodiment, the efficiency with respect to transmitting and receiving electric power is good.

In this connection, a configuration may be adopted in which the capacitance adjustment section 15D that the power supply apparatus 10H includes is used in combination with the configuration of any of the power supply apparatuses 10D to 10G.

Ninth Embodiment

Hereunder, a power supply system 1J of a ninth embodiment of the present invention is described. Since the power supply system 1J of the present embodiment is similar to the power supply systems and the power supply apparatuses of embodiments that are already described, like components are denoted by like reference symbols and a description of such components is omitted below.

Figure 18:
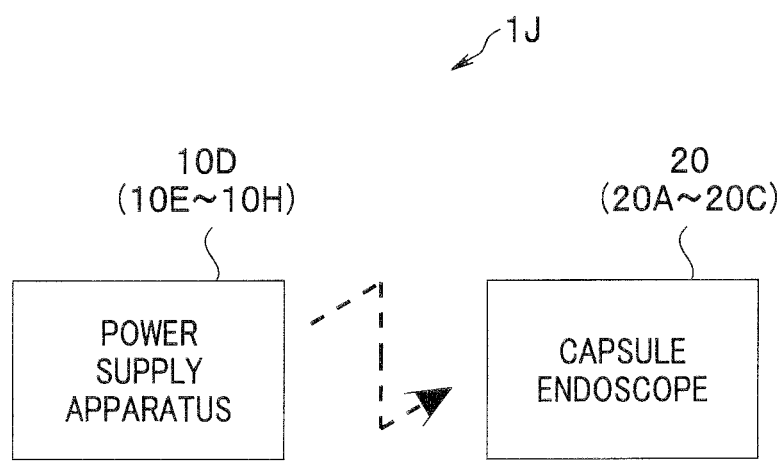
FIG. 18 is a configuration diagram that illustrates a configuration of a power supply apparatus system according to a ninth embodiment.

As shown in FIG. 2, FIG. 18, and FIG. 13, the power supply system 1J includes the capsule-type endoscope 20 that wirelessly receives an electric power from outside the body of the individual to be examined 50 and performs predetermined processing inside the body, and a power supply apparatus that wirelessly supplies an electric power from outside the body of the individual to be examined 50 to the capsule-type endoscope 20 inside the body. The capsule-type endoscope 20 includes the processing circuit 22 that performs predetermined processing inside the body, the power receiving coil 21 that receives an electric power from outside the body, and the power receiving circuit 22 that has the adjusting reactance section 23. By adjusting a reactance of the adjusting reactance section 23, the capsule-type endoscope 20 matches an impedance of the processing circuit 25 and an impedance of the power receiving circuit 25. The power supply apparatus 10D includes the power transmission coil 11D that generates an AC magnetic field, the power transmitting resonance capacitor 13 that is connected in series with the power transmission coil 11D, and the power transmission coil drive section 16 that drives the power transmission coil 11D. When the power transmission coil drive section 16 detects that a resonant state has been terminated by an abrupt fall in a driving current or an abrupt rise in a driving voltage, the power transmission coil drive section 16 performs control that matches the frequency of an AC magnetic field to a resonance frequency.

Since the power supply apparatus 10D efficiently transmits an electric power and the capsule-type endoscope 20 efficiently receives an electric power, in the power supply system 1J of the present embodiment, the efficiency with respect to transmitting and receiving an electric power is good.

Further, a configuration that combines any one of the capsule-type endoscopes 20, and 20A to 20C of the first to third embodiments and the modification example and any one of the power supply apparatuses 10D to 10H of the fourth to eighth embodiments may be adopted as the configuration of the power supply system 1J.

Furthermore, although in the above description a capsule-type endoscope is described as an example of a capsule-type medical device, the present invention can be applied to various kinds of capsule-type medical devices such as a capsule-type medical device for collecting digestive fluids, a swallowable pH sensor, or a drug delivery system.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A capsule-type medical device that receives an electric power from outside a body of an individual to be examined and performs a plurality of kinds of predetermined processing inside the body, comprising:

a processing circuit that performs the plurality of kinds of predetermined processing inside the body, a processing load for each of the plurality of kinds of predetermined processing being different; and a power receiving circuit that has a power receiving coil that wirelessly receives an electric power from outside the body, a power receiving resonance capacitor, and an adjusting reactance section that is capable of adjusting a reactance that is connected to the power receiving coil and the power receiving resonance capacitor;

wherein the capsule-type medical device further comprises a reactance adjusting circuit that matches an impedance of the processing circuit and an impedance of the power receiving circuit by adjusting a reactance of the adjusting reactance section, in accordance with each of the plurality of kinds of predetermined processing.

2. The capsule-type medical device according to claim 1, wherein the reactance adjusting circuit adjusts the reactance based on each of control signals for the plurality of kinds of predetermined processing.

3. The capsule-type medical device according to claim 2, wherein:

the adjusting reactance section has a plurality of power receiving reactance elements that have different reactances to each other, and a reactance adjustment switch section that switches the power receiving reactance element that connects to the power receiving coil; and the reactance adjusting circuit adjusts a reactance of the adjusting reactance section by switching the reactance adjustment switch section.

4. The capsule-type medical device according to claim 1, further comprising:

a load detection circuit that detects an impedance of the processing circuit;

wherein the reactance adjusting circuit adjusts a reactance of the adjusting reactance section in accordance with information detected by the load detection circuit.

5. The capsule-type medical device according to claim 4, wherein:

the adjusting reactance section has a plurality of power receiving reactance elements that have different reactances to each other, and a reactance adjustment switch section that switches the power receiving reactance element that connects to the power receiving coil; and the reactance adjusting circuit adjusts a reactance of the adjusting reactance section by switching the reactance adjustment switch section.

6. The capsule-type medical device according to claim 1, wherein the processing circuit has an illumination section that illuminates inside of a body.

7. A power supply apparatus that wirelessly supplies an electric power from outside a body of an individual to be examined to a capsule-type medical device that performs predetermined processing inside the body of the individual to be examined, comprising:

a power transmission coil that is disposed outside the body of the individual to be examined and that generates an AC magnetic field;

a power transmitting resonance capacitor that is connected in series to the power transmission coil; and a power transmission coil drive section that drives the power transmission coil;

wherein upon detecting a termination of a resonant state of the AC magnetic field by an abrupt fall in a driving current or an abrupt rise in a driving voltage, the power transmission coil drive section performs control that restores the AC magnetic field to a resonant state in which a frequency of the AC magnetic field is equal to a resonance frequency of a power receiving circuit of the capsule-type medical device;

wherein the power transmission coil changes in shape due to a change in a posture of the individual to be examined;

wherein upon detecting a termination of a resonant state of the AC magnetic field, the power transmission coil drive section performs control that changes an inductance of the power transmission coil;

wherein said power supply apparatus further comprising:

a coil length adjusting section that shortens a coil length of the power transmission coil; and wherein the power transmission coil drive section changes an inductance of the power transmission coil by means of the coil length adjusting section.

8. The power supply apparatus according to claim 7, further comprising:

a power transmitting inductance adjustment section that is provided between the power transmission coil and the power transmission coil drive section;

wherein the power transmission coil drive section restores the AC magnetic field to a resonant state by means of the power transmitting inductance adjustment section.

9. The power supply apparatus according to claim 7, further comprising:

a capacitance adjustment section that is provided between the power transmission coil and the power transmission coil drive section;

wherein the power transmission coil drive section restores the AC magnetic field to a resonant state by means of the capacitance adjustment section.

10. A power supply system comprising a capsule-type medical device and a power supply apparatus, in which:

the capsule-type medical device wirelessly receives an electric power from outside a body of an individual to be examined and performs a plurality of kinds of predetermined processing inside the body, and the power supply apparatus wirelessly supplies an electric power from outside the body of the individual to be examined to the capsule-type medical device that is inside the body, wherein:

the capsule-type medical device comprises:

a processing circuit that performs the plurality of kinds of predetermined processing inside the body, a processing load for each of the plurality of kinds of predetermined processing being different, and a power receiving circuit that is a resonant circuit with a predetermined resonance frequency that has a power receiving coil that receives an electric power from outside the body, a power receiving resonance capacitor, and an adjusting reactance section that is capable of adjusting a reactance that is connected to the power receiving coil and the power receiving resonance capacitor, wherein the capsule-type medical device further comprises
a reactance adjusting circuit that matches an impedance of the processing circuit and an impedance of the power receiving circuit by adjusting a reactance of the adjusting reactance section, in accordance with each of the plurality of kinds of predetermined processing; and
the power supply apparatus comprises:
a power transmission coil that generates an AC magnetic field,
a power transmitting resonance capacitor that is connected in series to the power transmission coil, and
a power transmission coil drive section that drives the power transmission coil,
wherein upon detecting a termination of a resonant state of the AC magnetic field by an abrupt fall in a driving current or an abrupt rise in a driving voltage, the power transmission coil drive section performs control that restores the AC magnetic field to a resonant state in which a frequency of the AC magnetic field is equal to a resonance frequency of a power receiving circuit of the capsule-type medical device.

11. The power supply system according to claim 10, wherein the capsule-type medical device further comprises:
a load detection circuit that detects an impedance of the processing circuit;
wherein the reactance adjusting circuit adjusts a reactance of the adjusting reactance section in accordance with the impedance of the processing circuit that the load detection circuit detects.

12. The power supply system according to claim 11, wherein the capsule-type medical device is a capsule-type endoscope apparatus that has an illumination section that illuminates the inside of the body.

13. The power supply system according to claim 10, wherein the reactance adjusting circuit adjusts the reactance based on each of control signals for the plurality of kinds of predetermined processing.

14. The power supply system according to claim 10, wherein the power transmission coil changes in shape due to a change in a posture of the individual to be examined.

* * * * *